(12) United States Patent
Shibamoto et al.

(10) Patent No.: US 7,224,104 B2
(45) Date of Patent: May 29, 2007

(54) ULTRASONIC PROBE AND ULTRASONIC DIAGNOSTIC APPARATUS

(75) Inventors: Koichi Shibamoto, Otawara (JP); Hiroyuki Shikata, Nasu-gun (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 72 days.

(21) Appl. No.: 11/004,946

(22) Filed: Dec. 7, 2004

(65) Prior Publication Data
US 2005/0122004 A1 Jun. 9, 2005

(30) Foreign Application Priority Data
Dec. 9, 2003 (JP) .............................. 2003-409786

(51) Int. Cl.
*H01L 41/08* (2006.01)
(52) U.S. Cl. ....................................... 310/335; 310/334
(58) Field of Classification Search ......... 310/334–337
See application file for complete search history.

(56) References Cited
U.S. PATENT DOCUMENTS

| | | | | |
|---|---|---|---|---|
| 4,348,904 A | 9/1982 | Bautista, Jr. | | |
| 4,523,122 A * | 6/1985 | Tone et al. | .................. | 310/334 |
| 5,375,099 A | 12/1994 | Gill | | |
| 5,423,220 A | 6/1995 | Finsterwald et al. | | |
| 5,884,627 A | 3/1999 | Wakabayashi et al. | | |
| 6,225,729 B1 | 5/2001 | Izumi et al. | | |
| 6,788,620 B2 * | 9/2004 | Shiraishi et al. | ............. | 367/152 |
| 6,969,943 B2 * | 11/2005 | Hashimoto et al. | ......... | 310/334 |
| 6,989,625 B2 * | 1/2006 | Suzuki et al. | ................ | 310/334 |

FOREIGN PATENT DOCUMENTS

| | | |
|---|---|---|
| EP | 0 346 891 A2 | 12/1989 |
| JP | 6-327098 | 11/1994 |
| JP | 2004-45389 | 2/2004 |

* cited by examiner

*Primary Examiner*—Mark Budd
(74) *Attorney, Agent, or Firm*—Oblon, Spivak, McClelland, Maier & Neustadt, P.C.

(57) ABSTRACT

An ultrasonic probe includes a piezoelectric oscillator layer having plural arranged piezoelectric oscillators for transmitting and receiving ultrasonic waves and plural electrodes formed in the piezoelectric oscillators, an acoustic lens for focusing or diffusing the ultrasonic waves, and an acoustic matching layer that is provided between the piezoelectric oscillator layer and the acoustic lens and includes a resin base and fine particles, which have electric conductivity, mixed in the resin base.

17 Claims, 5 Drawing Sheets

ULTRASONIC PROBE AND ULTRASONIC DIAGNOSTIC APPARATUS

CROSS-REFERENCE TO RELATED APPLICATIONS

This application is based upon and claims the benefit of priority from prior Japanese Patent Application No. 2003-409786, filed Dec. 9, 2003, the entire contents of which are incorporated herein by reference.

BACKGROUND OF THE INVENTION

1. Field of the Invention

The present invention relates to an ultrasonic probe and an ultrasonic diagnostic apparatus.

2. Description of the Related Art

There is known an ultrasonic diagnostic apparatus that scans the inside of a subject with an ultrasonic wave and visualizes an inside state of the subject on the basis of a reception signal generated from a reflected wave from the inside of the subject. Such an ultrasonic diagnostic apparatus transmits an ultrasonic wave into the subject with an ultrasonic probe including piezoelectric oscillators and receives a reflected wave, which is caused by mismatching of acoustic impedances in the subject, with the ultrasonic probe to generate a reception signal.

In the ultrasonic probe, plural piezoelectric oscillators, which oscillate on the basis of a transmission signal to generate an ultrasonic wave and receives a reflected wave to generate a reception signal, are arranged in a scanning direction. For example, such piezoelectric oscillators transmit an ultrasonic wave having a rectangular sound pressure distribution, which is uniform in a direction perpendicular to the scanning direction, and form a focus at a predetermined depth in a subject when the piezoelectric oscillators are given a differential delay by an acoustic lens.

Incidentally, for the purpose of realizing acoustic matching of an acoustic impedance of the piezoelectric oscillators and an acoustic impedance of the subject, an acoustic matching layer having a multilayer structure is provided on the piezoelectric oscillators to transmit and receive ultrasonic waves via the acoustic matching layer. As the acoustic matching layer, an acoustic matching layer consisting of two layers has more satisfactory acoustic matching than an acoustic matching layer consisting of one layer. An acoustic matching layer consisting of three layers has still more satisfactory acoustic matching. This is because an acoustic loss is less when acoustic impedances change from the piezoelectric oscillators to the subject in three stages than in one stage.

The acoustic matching between the piezoelectric oscillators and the subject is made satisfactory in this way. This is because, if a difference between the acoustic impedance of the piezoelectric oscillators and the acoustic impedance of the subject is large, a reflection loss of an ultrasonic wave in the subject increases when the ultrasonic wave is transmitted from the piezoelectric oscillators to the subject. Consequently, the transmission of the ultrasonic wave to the subject cannot be performed efficiently, and a high quality image cannot be obtained.

FIG. 9 shows a structure of an ultrasonic probe including an acoustic matching layer having a multilayer structure. FIG. 9 is a front view of the ultrasonic probe. The ultrasonic probe includes a back material 32, a piezoelectric oscillator layer 33 that is divided into plural layers to be arranged in a scanning direction on the back material 32, an acoustic matching layer 34 that is divided into plural layers to be arranged in the scanning direction on the piezoelectric oscillator layer 33, and an acoustic lens 35 provided on the acoustic matching layer 34. The acoustic matching layer 34 includes a first acoustic matching layer 34a, a second acoustic matching layer 34b provided on the first acoustic matching layer 34a, and a third acoustic matching layer 34c provided on the second acoustic matching layer 34b. In such an ultrasonic probe, the piezoelectric oscillator layer 33 performs transmission and reception of ultrasonic waves via the acoustic matching layer 34.

In general, an acoustic impedance of the piezoelectric oscillator layer 33 is about 30 Mrayl and an acoustic impedance of a subject is about 1.5 Mrayl. In order to make acoustic matching between the piezoelectric oscillator layer 33 and the subject, it is necessary to form the acoustic matching layer 4 in a multilayer structure and gradually reduce acoustic impedances from the piezoelectric oscillator layer 33 to the subject. In the case of the ultrasonic probe shown in FIG. 9, it is necessary to gradually reduce acoustic impedances from the first acoustic matching layer 34a to the third acoustic matching layer 34c to set an acoustic impedance of an acoustic matching layer on the subject side (the third acoustic matching layer 34c) of the acoustic matching layer 34 to 1.5 to 3.5 Mrayl. In addition, in the case of an ultrasonic probe including an acoustic matching layer consisting of two layers, it is necessary to set an acoustic impedance of the second acoustic matching layer to 1.5 to 3.5 Mrayl.

Conventionally, an acoustic impedance is set low by using a soft resin film of polyurethane or polyethylene in the acoustic matching layer 34. However, since the resin film is poor in machinability due to its flexibility, it is impossible to subject the acoustic matching layer 34 to machining by dice cutting (array machining) in order to divide the acoustic matching layer 34 into plural layers to be arranged in the scanning direction. In other words, after stacking the piezoelectric oscillator layer 33 and the acoustic matching layer 34 on the back material 2, it is impossible to subject the acoustic matching layer 34 to dice cutting at a desired pitch. Therefore, there is a problem in that acoustic crosstalk between the piezoelectric oscillator layer 33 and the acoustic matching layer 34 is high. In addition, since machinability is poor, it is impossible to manufacture the ultrasonic probe easily.

In addition, since polyurethane and polyethylene do not have electric conductivity, it is impossible to draw out a ground electrode from the acoustic matching layer 34 side. Here, even if conductive particles such as a metal filler is mixed in polyurethane or polyethylene in order to give electric conductivity to the acoustic matching layer 34, a desired acoustic impedance is not satisfied because a density of the acoustic matching layer 34 increases.

BRIEF SUMMARY OF THE INVENTION

It is an object of the invention to provide an ultrasonic probe that is easily machined.

In a first aspect of the invention, an ultrasonic probe includes: a piezoelectric oscillator layer having plural arranged piezoelectric oscillators for transmitting and receiving ultrasonic waves and plural electrodes formed in the piezoelectric oscillators; an acoustic lens for focusing or diffusing the ultrasonic waves; and an acoustic matching layer that is provided between the piezoelectric oscillator layer and the acoustic lens and includes a resin base and fine particles, which have electric conductivity, mixed in the resin base.

In a second aspect of the invention, an ultrasonic probe includes: a piezoelectric oscillator layer for transmitting and receiving ultrasonic waves; an acoustic lens for focusing or diffusing the ultrasonic waves; and plural acoustic matching layers stacked between the piezoelectric oscillator layer and the acoustic lens, wherein at least one of the plural acoustic matching layer includes a resin base and fine particles, which have electric conductivity, mixed in the resin base.

In a third aspect of the invention, an ultrasonic diagnostic apparatus includes: an ultrasonic probe; a scanning unit that scans a subject with an ultrasonic wave via the ultrasonic probe and collects plural echo signals from the subject; and an image generating unit that generates an internal image of the subject on the basis of the echo signals collected by the scanning unit, wherein the ultrasonic prove includes: a piezoelectric oscillator layer having plural arranged piezoelectric oscillators for transmitting and receiving ultrasonic waves and plural electrodes formed in the piezoelectric oscillators; an acoustic lens for focusing or diffusing the ultrasonic waves; and an acoustic matching layer that is provided between the piezoelectric oscillator layer and the acoustic lens and includes a resin base and fine particles, which have electric conductivity, mixed in the resin base.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

An ultrasonic probe in accordance with an embodiment of the invention will be hereinafter explained with reference to the accompanying drawings.

Figure 1:
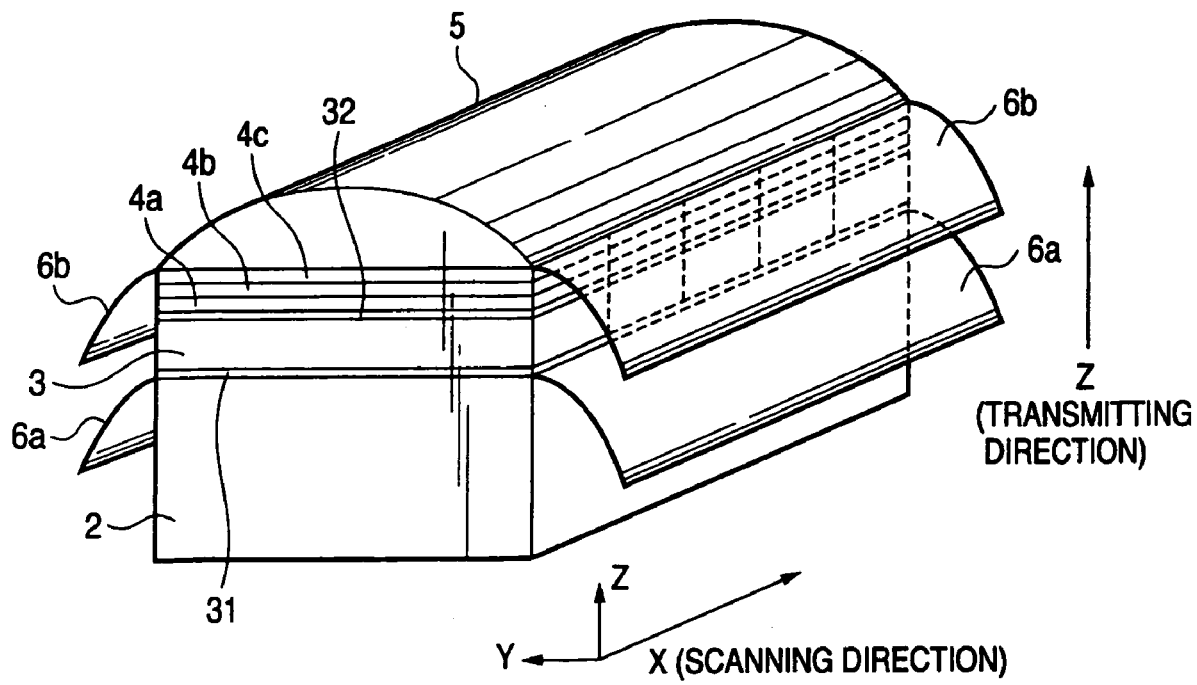
FIG. 1 is a perspective view showing a schematic structure of an ultrasonic probe in accordance with an embodiment of the invention.

FIG. 1 is a perspective view showing a schematic structure of the ultrasonic probe in accordance with the embodiment. The ultrasonic probe consists of a head side and a cable side. FIG. 1 shows the head side of the ultrasonic probe.

Figure 3:
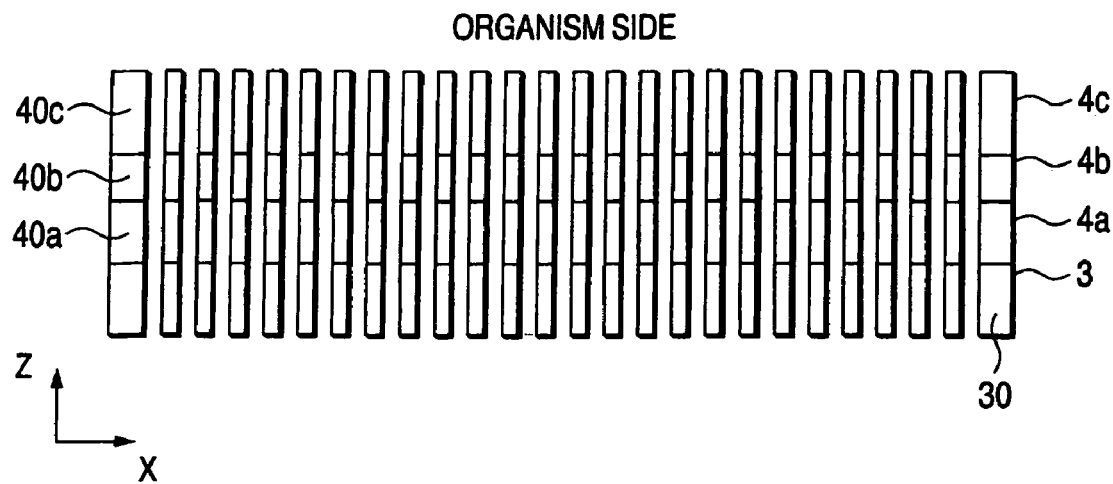
FIG. 3 is an XZ sectional view of the ultrasonic probe in FIG. 1.

As shown in FIG. 1, an ultrasonic probe 1 in accordance with this embodiment includes a back material 2, a piezoelectric oscillator layer 3 on the back material 2, an acoustic matching layer 4 multilayered along a transmitting direction Z on the piezoelectric oscillator layer 3, and an acoustic lens 5 for focusing or diffusing ultrasonic waves provided on the acoustic matching layer 4. As shown in FIG. 3, the piezoelectric oscillator layer 3 has plural piezoelectric oscillators 30 arranged along a scanning direction X.

The acoustic matching layer 4 includes a first acoustic matching layer 4a, a second acoustic matching layer 4b provided on the first acoustic matching layer 4a, and a third acoustic matching layer 4c provided on the second acoustic matching layer 4b. The first to the third acoustic matching layers 4a, 4b, and 4c are stacked on the piezoelectric oscillator layer 3. All the first to the third acoustic matching layers 4a, 4b, and 4c have electric conductivity. Consequently, it is possible to draw out a ground electrode 32 via the first to the third acoustic matching layers 4a, 4b, and 4c. In other words, it is possible to draw out the ground electrode 32 from a part between the acoustic matching layer 4 and the acoustic lens 5.

The first acoustic matching layer 4a has an acoustic impedance lower than that of the piezoelectric oscillator layer 3 and higher than that of the second acoustic matching layer 4b. The second acoustic matching layer 4b has an acoustic impedance lower than that of the first acoustic matching layer 4a and higher than that of the third acoustic matching layer 4c. The third acoustic matching layer 4c has an acoustic impedance lower than that of the second acoustic matching layer 4b and higher than that of the subject.

The piezoelectric oscillator layer 3 is divided along the scanning direction X. Similarly, the first, the second, and the third acoustic matching layers 4a, 4b, and 4c are divided along the scanning direction X, respectively. In other words, the first acoustic matching layer 4a has plural first acoustic matching elements 40a arranged along the scanning direction X. The plural first acoustic matching elements 40a correspond to the plural piezoelectric oscillators 30, respectively. The second acoustic matching layer 4b has plural second acoustic matching elements 40b arranged along the scanning direction X. The plural second acoustic matching elements 40b correspond to the plural first acoustic matching elements 40a, respectively. The third acoustic matching layer 4c has plural third acoustic matching elements 40c arranged along the scanning direction X. The plural third acoustic matching elements 40c correspond to the plural second acoustic matching elements 40b, respectively.

The respective piezoelectric oscillators 30 are separated from the adjacent piezoelectric oscillators 30 physically and acoustically. The respective first acoustic matching elements 40a are also separated from the adjacent first acoustic matching elements 40a physically and acoustically. The respective second acoustic matching elements 40b are also separated from the adjacent second acoustic matching elements 40b physically and acoustically. The respective third acoustic matching elements 40c are also separated from the adjacent third acoustic matching elements 40c physically and acoustically. Conventionally, since the third acoustic matching layer is not divided, interference occurs between the piezoelectric oscillators 30 adjacent to each other via the third acoustic matching layer. In the invention, since the respective third acoustic matching elements 40c are also separated from the adjacent third acoustic matching elements 40c physically and acoustically, interference between the piezoelectric oscillators 30 adjacent to each other does not occur substantially.

The back material 2 attenuates and absorbs ultrasonic oscillation components, which are not necessary for image extraction of the ultrasonic diagnostic apparatus, in ultrasonic oscillation generated from the piezoelectric oscillator layer 3 or ultrasonic oscillation at the time of reception.

The piezoelectric oscillator 30 consists of, for example, a ceramic material such as lead zirconate titanate Pb(Zr,Ti)O3, lithium niobate (LiNbO3), barium titanate (BaTiO3), or lead titanate (PbTiO3). In addition, an electrode 31 and an electrode 32 are formed on both upper and lower layers of the piezoelectric oscillator layer 3. Typically, the electrode 31 is a signal electrode and the electrode 32 is a common electrode (ground electrode).

In addition, by multilayering the acoustic matching layer 4, occurrence of a signal loss due to a difference of acoustic impedance between the acoustic matching layer 4 and a body surface of the subject is controlled in conjunction with the acoustic lens 5. A structure of this acoustic matching layer 4 will be described in detail later.

The acoustic lens 5 comes into contact with the body surface of the subject and mediates transmission and reception of ultrasonic waves. An acoustic focus in a slice direction is formed at a predetermined depth from the body surface by the acoustic lens 5. In addition, an acoustic focus in a scanning direction is formed by controlling to switch transmission and reception timing of the plural piezoelectric oscillators 30 arranged in a strip shape in the scanning direction.

Figure 4:
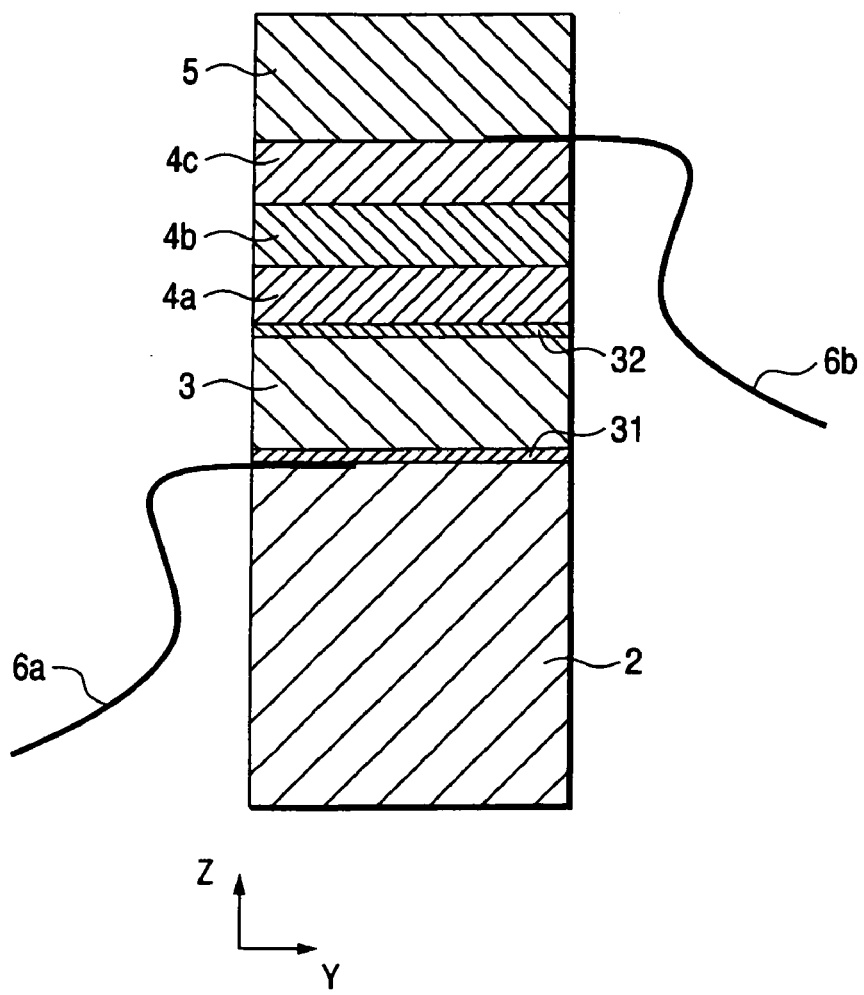
FIG. 4 is a YZ sectional view of the ultrasonic probe in FIG. 1.

As shown in FIG. 4, a flexible substrate 6a for drawing out a signal electrode having a Cu foil formed on an entire surface thereof is bonded between the back material 2 and the piezoelectric oscillator layer 3 via the electrode 31. Moreover, a flexible substrate 6b for drawing out a ground electrode is provided between the acoustic matching layer 4 and the acoustic lens 5. More specifically, the flexible substrate 6b is provided between the third acoustic matching layer 4c and the acoustic lens 5. Note that the flexible substrate 6a plays a role of a lead wire.

Figure 2A:
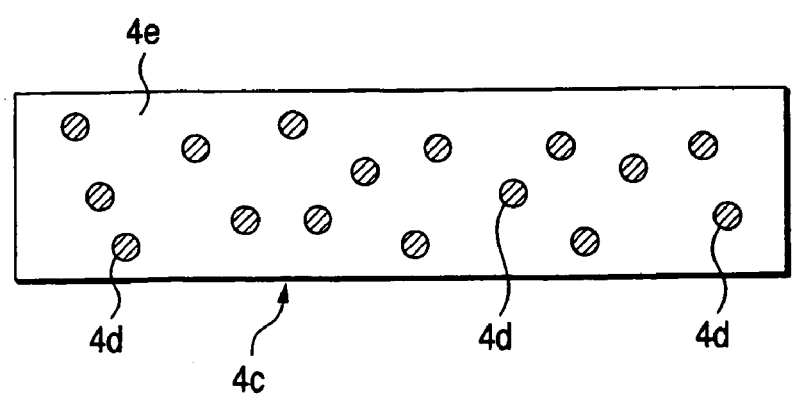
FIG. 2A is a sectional view of a third acoustic matching layer in FIG. 1.

Next, the acoustic matching layer 4 of the ultrasonic probe 1 in accordance with this embodiment will be explained in detail. In the ultrasonic probe in accordance with this embodiment, since the third acoustic matching layer 4c comes into contact with the subject via the acoustic lens 5, this third acoustic matching layer 4c is required to have an acoustic impedance of about 2 Mrayl. First, a structure of the third acoustic matching layer 4c will be explained with reference to FIGS. 2A and 2B. FIG. 2A is a sectional view of the third acoustic matching layer 4c.

The third acoustic matching layer 4c includes a resin base 4e and hollow fine particles 4d mixed in the resin base 4e. A particle diameter of the fine particles 4d is 40 nm. The fine particles 4d have a porosity of 60%. Typically, a shell material of the fine particles 4d is formed of conductive carbon or gold. The resin base 4e is formed of, for example, epoxy resin or urethane resin with an acoustic impedance of about 3 Mrayl. The acoustic impedance can be lowered by mixture of the fine particles 4d. This makes it possible to adopt the resin base 4e of epoxy or urethane, which has a relatively high acoustic impedance but has a relatively high hardness, in the third acoustic matching layer 4c. Consequently, it is possible to cut the third acoustic matching layer 4c in the same manner as the piezoelectric oscillator layer 3, the first acoustic matching layer 4a, and the second acoustic matching layer 4b. As a material of the conventional third acoustic matching layer, extremely soft resin is inevitably adopted in order to acquire a low acoustic impedance.

Figure 2B:
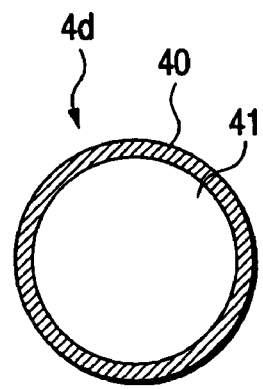
FIG. 2B is a sectional view of a fine particle in FIG. 2A.

As shown in FIG. 2B, the fine particle 4d is formed by encapsulating a gas 41, typically, the air in a shell 40 of, for example, carbon having electric conductivity. The shell 40 has an acoustic impedance higher than that of the resin base 4e. An inside 41 of the shell 40 has an acoustic impedance lower than that of the resin base 4e. Instead of encapsulating the gas 41 in the shell 40, the shell 40 may be coated with a solid having a characteristic that an acoustic impedance thereof is lower than that of the resin base 4e.

A particle diameter of the fine particle 4d relates to a wavelength of an ultrasonic wave to be transmitted and received. If the particle diameter of the fine particle 4d is too large, the ultrasonic wave is reflected by the fine particle 4 and scatters. For example, when the size of the particle diameter of the fine particle 4d is reduced to a size ⅕ to ¹/₁₀ or less as small as a wavelength of an ultrasonic wave, reflection and scattering of the ultrasonic wave do not occur substantially. Here, an acoustic velocity in epoxy resin is 2500 m/s. In this embodiment, an ultrasonic wave with a frequency of 5 MHz is used, a wavelength is assumed to be about 500 μs, and reflection and scattering of the ultrasonic wave are not observed. Reflection and scattering of the ultrasonic wave are less likely to occur as the particle diameter of the fine particle 4d is smaller.

Figure 5:
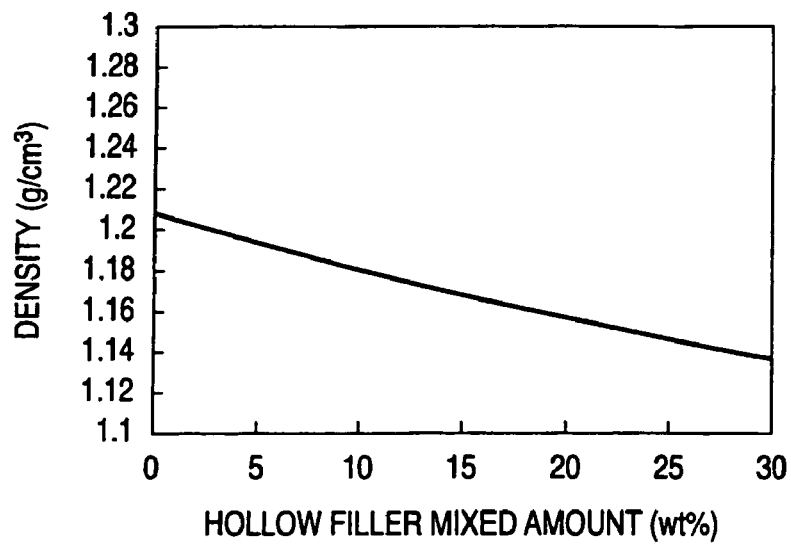
FIG. 5 is a graph representing a relation between a mixed amount of a hollow carbon filler and a density of an acoustic matching layer in the embodiment.
Figure 6:
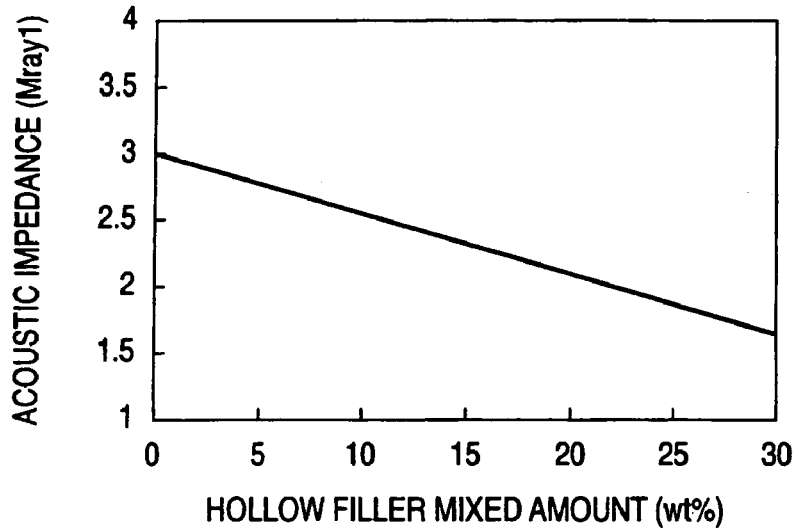
FIG. 6 is a graph representing a relation between a mixed amount of a hollow carbon filler and an acoustic impedance of the acoustic matching layer in the embodiment of the invention.

Changes in a density and an acoustic impedance of the third acoustic matching layer 4c in the case in which a hollow carbon filler is mixed in the third acoustic matching layer 4 will be explained with reference to FIGS. 5 and 6. FIG. 5 is a graph representing a relation between a mixed amount of a hollow carbon filler and a density of the third acoustic matching layer 4c. FIG. 6 is a graph representing a mixed amount of a hollow carbon filler and an acoustic impedance of the third acoustic matching layer 4c. As shown in FIG. 5, when the mixed amount of the hollow carbon filler is increased, the density of the third acoustic matching layer 4c falls. In addition, as shown in FIG. 6, when the mixed amount of the hollow carbon filler is increased, the acoustic impedance of the third acoustic matching layer 4c falls. In this way, a proportional relation is established between a density and an acoustic impedance of an acoustic matching layer, and it is possible to lower the acoustic impedance of the third acoustic matching layer 4c by mixing the hollow carbon filler in the third acoustic matching layer 4c to reduce the density of the third acoustic matching layer 4c. For example, it is possible to lower the acoustic impedance of the third acoustic matching layer 4c to about 2 Mrayl by reducing the mixed amount of the hollow carbon filler to about 20 wt %.

If a carbon filler having a porosity higher than 60% is used, it is possible to obtain an acoustic impedance of about 2 Mrayl with a mixed amount of the carbon filler smaller than about 20 wt %. This is because the density of the third acoustic matching layer 4c falls even if the mixed amount is the same by raising the porosity. On the other hand, when a carbon filler with a porosity lower than 60% is used, it is possible to obtain an acoustic impedance of about 2 Mrayl with a mixed amount of the carbon filler larger than about 20 wt %. In this way, even in the case in which the porosity of the fine particles 4d (carbon filler) is changed, it is possible to obtain a desired acoustic impedance by adjusting a mixed amount of the fine particles 4d.

Figure 7:
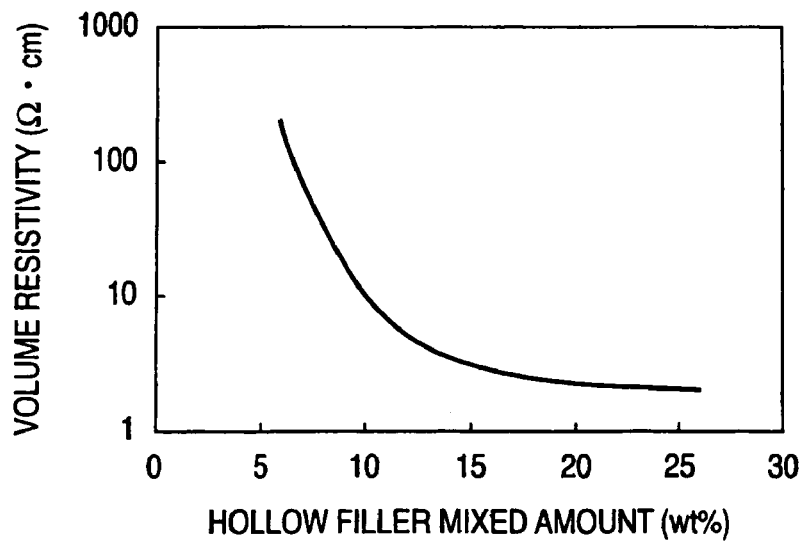
FIG. 7 is a graph representing a relation between a mixed amount of a hollow carbon filler and a volume resistivity of the acoustic matching layer in the embodiment of the invention.

A change in a volume resistivity of the third acoustic matching layer 4c in the case in which a hollow carbon filler is mixed in the third acoustic matching layer 4c will be explained with reference to FIG. 7. FIG. 7 is a graph representing a relation between a mixed amount of the hollow carbon filler and the volume resistivity of the third acoustic matching layer 4c.

Since the carbon filler (fine particles 4d) has electric conductivity, as shown in FIG. 7, when the mixed amount (volume ratio) with respect to the base 4e is increased, the volume resistivity of the third acoustic matching layer 4c decreases. Consequently, it is possible to give electric conductivity to the third acoustic matching layer 4c. As shown in the figure, when the mixed amount of the hollow carbon filler is increased to about 20 wt % or more, the volume resistivity falls to about 2 Ω·cm or less. Thus, it is possible to give sufficient electric conductivity to the third acoustic matching layer 4c.

Note that, when the mixed amount of the hollow carbon filler is increased in order to obtain electric conductivity, it is likely that the density of the third acoustic matching layer 4c falls to be too low and a desired acoustic impedance (an acoustic impedance of about 2 Mrayl) cannot be obtained. In such a case, a solid carbon filler may be mixed in the third acoustic matching layer 4c together with the hollow carbon filler to adjust the density of the third acoustic matching layer 4c to obtain the desired acoustic impedance.

In addition, a conductive material, for example, carbon graphite is used for the first acoustic matching layer 4a and the second acoustic matching layer 4b.

In this way, although the third acoustic matching layer 4c is formed of resin, conductive fine particles are mixed in the third acoustic matching layer 4c to give electric conductivity thereto. Consequently, it is possible to electrically connect the flexible substrate 6b for drawing out a ground electrode and the piezoelectric oscillator 30.

In this embodiment, the third acoustic matching layer 4c, which is one acoustic matching layer among the three acoustic matching layers, is formed of resin, and hollow fine particles are fixed in the third acoustic matching layer 4c to lower an acoustic impedance thereof. However, the invention is not limited to this. It is also possible that two or three acoustic matching layers among the three acoustic matching layers are formed of epoxy resin or urethan resin and the hollow fine particles 4e are mixed in the acoustic matching layers. In other words, it is also possible that not only the third acoustic matching layer 4c but also the second acoustic matching layer 4b and the first acoustic matching layer 4a are formed of resin and the hollow fine particles are mixed in the second acoustic matching layer 4b and the first acoustic matching layer 4a.

For example, when two acoustic matching layers among three acoustic matching layers are formed of resin, the third acoustic matching layer 4c and the second acoustic matching layer 4b are formed of resin and the hollow fine particles are mixed in the third acoustic matching layer 4c and the second acoustic matching layer 4b to lower acoustic impedances thereof. Here, a mixing amount of the hollow fine particles mixed in the third acoustic matching layer 4c is set larger than a mixing amount of the fine particle mixed in the second acoustic matching layer 4b to set an acoustic impedance of the third acoustic matching layer 4c low compared with an acoustic impedance of the second acoustic matching layer 4b. Consequently, it is possible to lower acoustic impedance of the acoustic matching layers gradually from the piezoelectric oscillator layer 3 to the subject and make acoustic matching between the piezoelectric oscillator layer 3 and the subject satisfactory.

The same holds true for the case in which all the three acoustic matching layers are formed of resin. A mixing amount of the fine particles mixed in the second acoustic matching layer 4b is set larger than a mixing amount of the fine particles mixed in the first acoustic matching layer 4a, and a mixing amount of the fine particles mixed in the third acoustic matching layer 4c is set larger than the mixing amount of the fine particles mixed in the second acoustic matching layer 4b. Consequently, an acoustic impedance of the second acoustic matching layer 4b is lower than an acoustic impedance of the first acoustic matching layer 4a, and an acoustic impedance of the third acoustic matching layer 4c is lower than the acoustic impedance of the second acoustic matching layer 4b. Therefore, it is possible to lower acoustic impedances of acoustic matching layers gradually from the piezoelectric oscillator layer 3 to the subject and make acoustic matching between the piezoelectric oscillator layer 3 and the subject satisfactory.

In addition, in this embodiment, the acoustic matching layer consisting of three layers is explained. However, the invention is not limited to this, and the acoustic matching layer 4 may be constituted by two layers or four or more layers. In such a case, it is possible to make acoustic matching satisfactory by lowering acoustic impedances of acoustic matching layers gradually from the piezoelectric oscillator layer 3 to the subject.

Note that, in this embodiment, the carbon filler is used as the hollow fine particles. However, the hollow fine particles are not limited to the carbon filler and any hollow fine particles such as an Au filler may be used as long as the hollow fine particles have electric conductivity. In addition, although the epoxy resin is used as resin in this embodiment, urethane resin may be used.

As described above, it is possible to make acoustic matching between the piezoelectric oscillator layer 3 and the subject satisfactory by lowering an acoustic impedance of an acoustic matching layer on the subject side.

Next, a method of manufacturing the ultrasonic probe 1 in accordance with this embodiment will be explained. First, a hollow carbon filler is mixed in epoxy resin and degassed and, then, the epoxy resin is applied on the second acoustic matching layer 4b. Then, the epoxy resin is heated and hardened and, then, polished to a desired thickness to form the third acoustic matching layer 4c.

In addition, it is also possible that the hollow carbon filler is mixed in the epoxy resin and, then, the epoxy resin is heated and hardened to prepare an ingot. In that case, the ingot is cut into a desired size and polished to a desired thickness to prepare the third acoustic matching layer 4c, which is bonded on the second acoustic matching layer 4b.

Then, the piezoelectric oscillator 3 is bonded on the back material 2 via the flexible substrate 6a, and the acoustic matching layer 4 is bonded on the piezoelectric oscillator 3. In this acoustic matching layer 4, the second acoustic matching layer 4b is bonded on the first acoustic matching layer 4a in advance, and the third acoustic matching layer 4c is bonded on the second acoustic matching layer 4b according to the method described above. Thereafter, the piezoelectric oscillator 3 and the acoustic matching layer 4 are subjected to dice cutting at a desired pitch to prepare the piezoelectric oscillator 3 and the acoustic matching layer 4 that are divided into plural layers in the scanning direction. Then, the acoustic lens 5 is bonded on the third acoustic matching layer 4c via the flexible substrate 6b to prepare the ultrasonic probe 1.

In this way, since machinability is improved by using the epoxy resin with relatively high hardness, it is possible to divide the piezoelectric oscillator 3 and the plural stacked acoustic matching layers 4 with dice cutting. In other word, since the ultrasonic probe in accordance with this embodiment can be subjected to array machining, it is possible reduce acoustic crosstalk compared with the conventional ultrasonic probe that cannot be subjected to array machining because the soft resin sheet with poor machinability is used. Moreover, since the material with relatively high hardness and satisfactory machinability is used, it is easy to machine the material and manufacture the ultrasonic probe 1.

Figure 8:
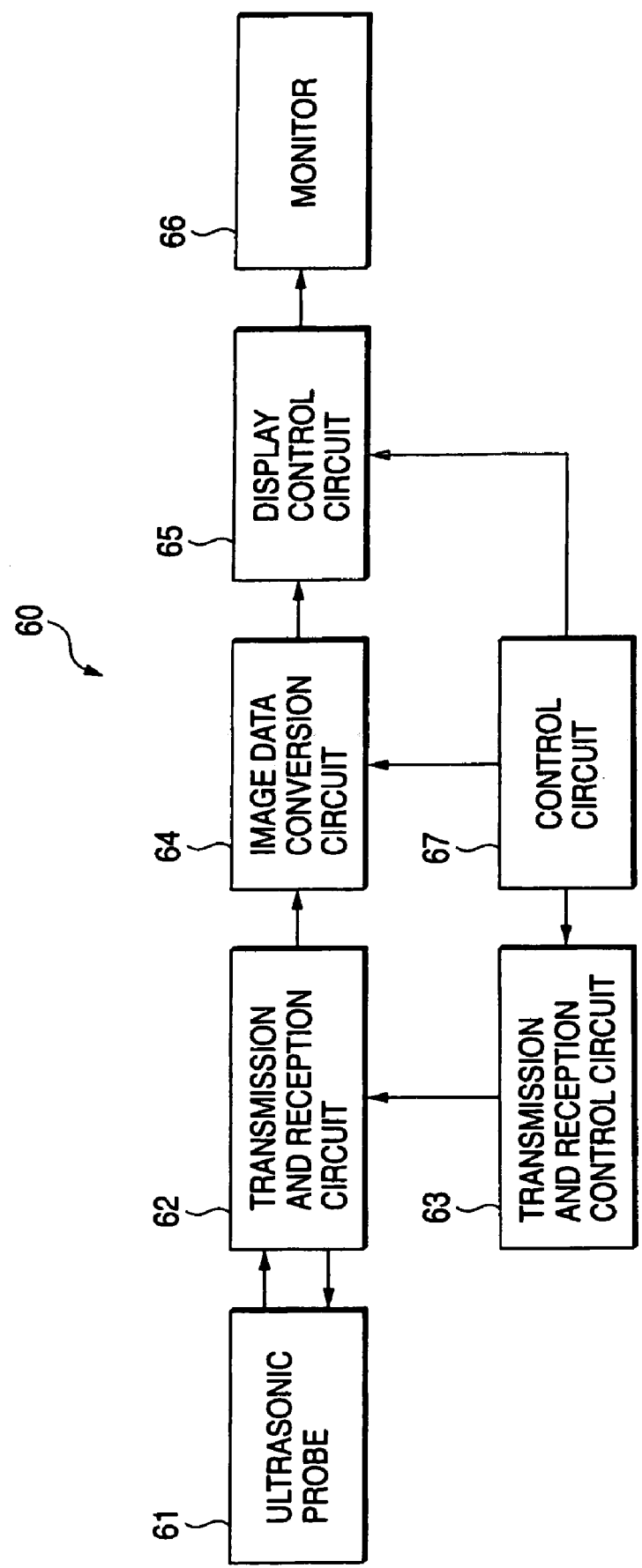
FIG. 8 is a block diagram showing a schematic structure of an ultrasonic diagnostic apparatus including the ultrasonic probe of the invention.
Figure 9:
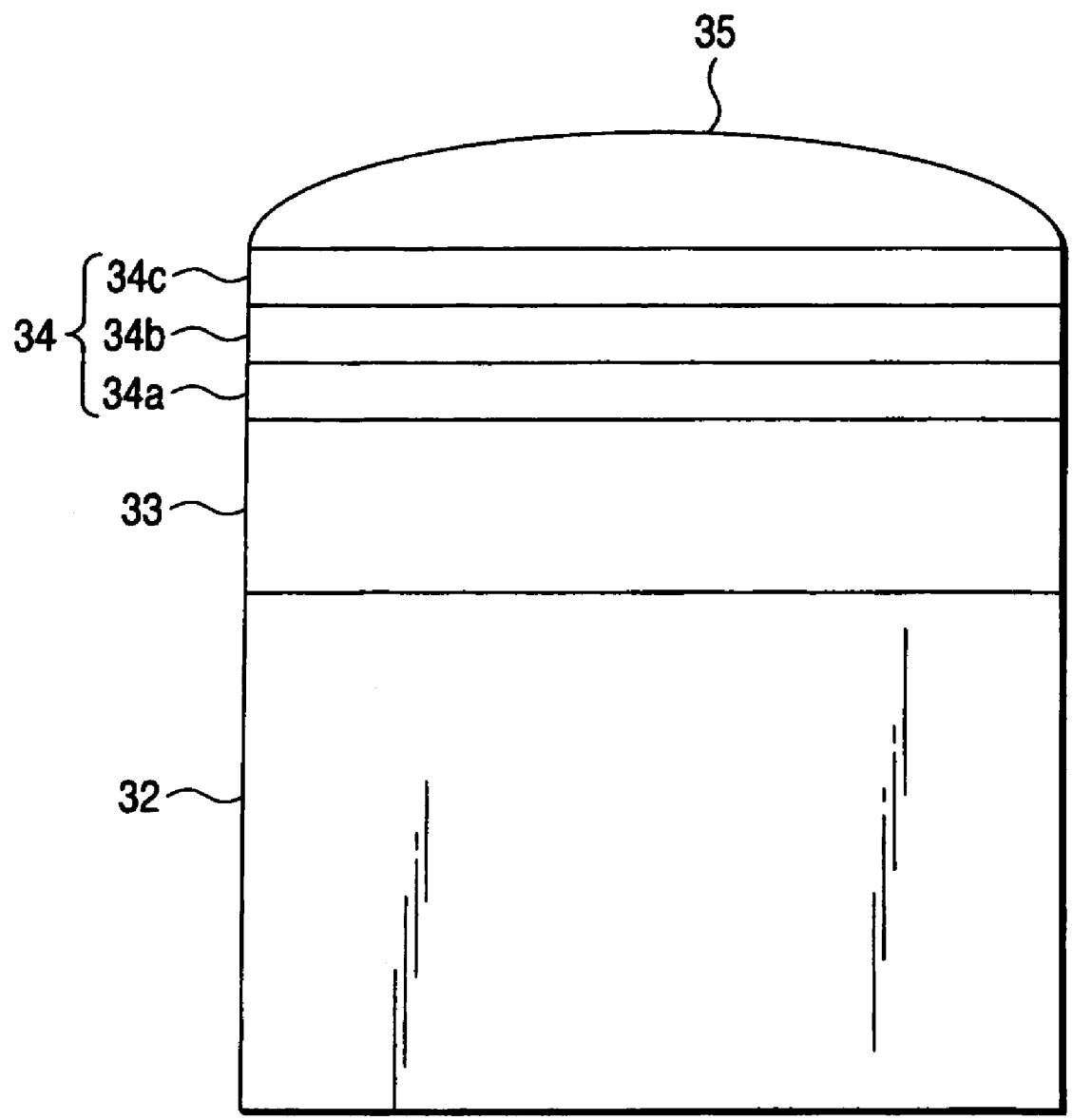
FIG. 9 is a sectional view of a conventional acoustic matching layer.

Next, an ultrasonic diagnostic apparatus including the ultrasonic probe of the invention will be explained with reference to FIG. 8. FIG. 8 is a block diagram showing a structure of a main part of an ultrasonic diagnostic apparatus in accordance with an embodiment of the invention.

This ultrasonic diagnostic apparatus 60 includes an ultrasonic probe 61, a transmission and reception circuit 62, a transmission and reception control circuit 63, an image data conversion circuit 64, a display control circuit 65, and a control circuit 67. The transmission and reception circuit 62 and the transmission and reception control circuit 63 are provided in order to scan a subject with an ultrasonic wave via the ultrasonic probe 61 and collect plural echo signals from the subject. The image data conversion circuit 64 is provided in order to generate an internal image of the subject on the basis of the echo signals collected by the scanning.

The ultrasonic probe of the invention is used as the ultrasonic probe 61. The ultrasonic probe 61 transmits an ultrasonic wave to a subject such as a patient and receives the ultrasonic wave reflected on the subject as an echo signal.

The transmission and reception circuit 62 supplies an electric signal to the ultrasonic probe 61 to generate an ultrasonic wave and receives the echo signal received by the ultrasonic probe 61. The transmission and reception control circuit 63 performs transmission and reception control for the transmission and reception circuit 62.

The image data conversion circuit 64 converts the echo signal received by the transmission and reception circuit 62 into ultrasonic image data of the subject. The display control circuit 65 controls a monitor 66 to display the ultrasonic image data converted by the image data conversion circuit 64. In addition, the control circuit 67 controls the entire ultrasonic diagnostic apparatus 60.

The transmission and reception control circuit 63, the image data conversion circuit 64, and the display control circuit 65 are connected to the control circuit 67, and the control circuit 67 controls operations of these respective circuits.

The control circuit 67 applies an electric signal to piezoelectric oscillators of the ultrasonic probe 61, sends the ultrasonic wave to the subject, and receives a reflected wave, which is caused by mismatching of acoustic impedances inside the subject, in the ultrasonic probe 61.

According to the ultrasonic diagnostic apparatus including the ultrasonic probe of the invention, acoustic matching of the piezoelectric oscillator 3 and the subject can be made satisfactory. Thus, it is possible to reduce a reflection loss of an ultrasonic wave and perform transmission of the ultrasonic wave to the subject efficiently. Consequently, it is possible to obtain a high quality image.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claim is:

1. An ultrasonic probe comprising:
a piezoelectric oscillator layer having plural arranged piezoelectric oscillators for transmitting and receiving ultrasonic waves and plural electrodes formed in the piezoelectric oscillators;
an acoustic lens for focusing or diffusing the ultrasonic waves; and
an acoustic matching layer that is provided between the piezoelectric oscillator layer and the acoustic lens and includes a resin base and fine particles, which have electric conductivity, mixed in the resin base; and
a substrate positioned between the acoustic matching layer and the acoustic lens, and extending out from the acoustic matching layer and the acoustic lens.

2. An ultrasonic probe according to claim 1, wherein the acoustic matching layer includes plural acoustic matching elements.

3. An ultrasonic probe according to claim 1, wherein the fine particles are hollow.

4. An ultrasonic probe according to claim 1, wherein the fine particles have an acoustic impedance lower than that of the resin base.

5. An ultrasonic probe according to claim 1, wherein the fine particles have a particle diameter $1/10$ as small as a wavelength of the ultrasonic waves.

6. An ultrasonic probe according to claim 1, wherein the fine particles include a shell material encapsulating a gas, the shell material having electric conductivity.

7. An ultrasonic probe according to claim 1, wherein the fine particles include a solid coated with a shell material having electric conductivity.

8. An ultrasonic probe according to claim 6, wherein the shell material is formed of carbon.

9. An ultrasonic probe according to claim 6, wherein the shell material is formed of gold.

10. An ultrasonic probe according to claim 1, wherein the resin base is formed of epoxy resin or urethane resin.

11. An ultrasonic probe according to claim 1, wherein at least one of the electrodes is drawn out from the substrate between the acoustic matching layer and the acoustic lens.

12. An ultrasonic probe according to claim 1, further comprising another acoustic matching layer that is provided between the piezoelectric oscillator layer and the acoustic matching layer and has an acoustic impedance higher than that of the acoustic matching layer.

13. An ultrasonic probe according to claim 1, wherein the acoustic matching layer has an acoustic impedance of 1.5 to 3.5 Mrayl.

14. An ultrasonic probe according to claim 1, wherein the acoustic matching layer has a volume resistivity of 2 Ω·cm or less.

15. An ultrasonic probe comprising:
a piezoelectric oscillator layer for transmitting and receiving ultrasonic waves;
an acoustic lens for focusing or diffusing the ultrasonic waves; and
plural acoustic matching layers stacked between the piezoelectric oscillator layer and the acoustic lens, wherein at least one of the plural acoustic matching layer includes a resin base and fine particles, which have electric conductivity, mixed in the resin base; and
a substrate positioned between the acoustic matching layer and the acoustic lens, and extending out from the acoustic matching layer and the acoustic lens.

16. An ultrasonic diagnostic apparatus comprising:
an ultrasonic probe;
a scanning unit that scans a subject with an ultrasonic wave via the ultrasonic probe and collects plural echo signals from the subject; and
an image generating unit that generates an internal image of the subject on the basis of the echo signals collected by the scanning unit, wherein
the ultrasonic prove includes:
a piezoelectric oscillator layer having plural arranged piezoelectric oscillators for transmitting and receiving ultrasonic waves and plural electrodes formed in the piezoelectric oscillators;
an acoustic lens for focusing or diffusing the ultrasonic waves; and
an acoustic matching layer that is provided between the piezoelectric oscillator layer and the acoustic lens and includes a resin base and fine particles, which have electric conductivity, mixed in the resin base; and
a substrate positioned between the acoustic matching layer and the acoustic lens, and extending out from the acoustic matching layer and the acoustic lens.

17. An ultrasonic probe according to claim 7, wherein the solid has an acoustic impedance less than that of the resin base.

* * * * *